US008158667B2

(12) United States Patent
Kador et al.

(10) Patent No.: US 8,158,667 B2
(45) Date of Patent: Apr. 17, 2012

(54) TOPICAL TREATMENT OF CATARACTS IN DOGS

(76) Inventors: Peter F. Kador, Omaha, NE (US); Milton Wyman, Powell, OH (US); Daniel M. Betts, Boone, IA (US)

( * ) Notice: Subject to any disclaimer, the term of this patent is extended or adjusted under 35 U.S.C. 154(b) by 878 days.

(21) Appl. No.: 11/892,307

(22) Filed: Aug. 21, 2007

(65) Prior Publication Data
US 2009/0082415 A1 Mar. 26, 2009

Related U.S. Application Data

(60) Provisional application No. 60/838,874, filed on Aug. 21, 2006.

(51) Int. Cl.
*A01N 43/52* (2006.01)
(52) U.S. Cl. ...................................................... 514/387
(58) Field of Classification Search .................. 514/387
See application file for complete search history.

(56) References Cited

U.S. PATENT DOCUMENTS

| | | | |
|---|---|---|---|
| 4,130,714 A | 12/1978 | Sarges | |
| 4,451,477 A | 5/1984 | Silvestrini et al. | |
| 4,540,704 A | 9/1985 | Ueda et al. | |
| 4,771,130 A | 9/1988 | Cohen | |
| 4,780,472 A | 10/1988 | Ueda et al. | |
| 4,797,422 A | 1/1989 | Testa | |
| 4,841,079 A | 6/1989 | Urban | |
| 4,873,255 A | 10/1989 | Yoshioka et al. | |
| 4,874,869 A | 10/1989 | Ueda et al. | |
| 4,911,920 A * | 3/1990 | Jani et al. ................... | 424/78.04 |
| 5,252,571 A | 10/1993 | Aotsuka et al. | |
| 5,294,635 A | 3/1994 | Eggler et al. | |
| 5,866,578 A * | 2/1999 | Mylari et al. ................ | 514/256 |
| 6,399,655 B1 | 6/2002 | de Juan, Jr. | |
| 6,476,039 B1 | 11/2002 | Ueno et al. | |
| 6,916,824 B1 | 7/2005 | Hua et al. | |
| 2003/0203966 A1 | 10/2003 | Collonges et al. | |
| 2005/0004225 A1 | 1/2005 | Balendiran | |

OTHER PUBLICATIONS

Randall Olson, et al, Cataract Treatment in the Beginning of the 21st Century, 136 Am. J. Ophthalmol. 146, 147 (Jul. 2003).*
Sanai Sato, et al, Progression of Sugar Cataract in the Dog, 32 Inv. Ophthalmol. Vis. Sci. 1925 (May 1991).*
Tian-Sheng Hu, et al, Reversal of Galactose Cataract with Sorbinil in Rats, 24 Invest. Ophthalmol. Vis. Sci. 640, 642-43 (May 1983).*
Datiles et al., "Corneal Re-epithelialization in Galactosemic Rats," Investigative Ophthalmology & Visual Science, vol. 24, May 1983, pp. 563-569.
Akagi et al., "Repair of corneal endothelium in galactosemic rats," Polyol Pathway and its Role in Diabetic Complications (Sakamoto et al., eds.) Elsevier Science Publishers BV (1988), pp. 237-243.
Kador et al., "The role of aldose reductase in the development of diabetic complications," Polyol Pathway and its Role in Diabetic Complications (Sakamoto et al., eds.) Elsevier Science Publishers BV (1988), pp. 20-31.

Kador et al., "Prevention of Retinal Vessel Changes Associated With Diabetic Retinopathy in Galactose-Fed Dogs by Aldose Reductase Inhibitors," Archives of Ophthalology, vol. 108, Sep. 1990, pp. 1301-1309.
Datiles et al., "The Effects of Sorbinil, an Aldose Reductase Inhibitor, on the Corneal Endothelium in Galactosemic Dogs," Investigative Ophthalmology & Visual Science, vol. 31, No. 11, Nov. 1990, pp. 2201-2204.
Sato et al., "Progression of Sugar Cataract in the Dog," Investigative Ophthalmology & Visual Science, vol. 32, No. 5, May 1991, pp. 1925-1931.
Neuenschwander et al., Dose-Dependent Reduction of Retinal Vessel Changes Associated with Diabetic Retinopathy in Galactose-Fed Dogs by the Aldose Reductase Inhibitor M79175, Journal of Ocular Pharmacology and Therapeutics, vol. 13, No. 6, 1997, pp. 517-528.
Sato et al., "Dose-Dependent Prevention of Sugar Cataracts in Galactose-fed Dogs by the Aldose Reductase Inhibitor M79175," Exp. Eye Res., vol. 66, (1998), pp. 217-222.
Caspers et al., "Iris Vasculopathy in Galactose-fed Rats," Exp. Eye Res., vol. 68 (1999), pp. 211-221.
Kador et al., "Effects of topical administration of an aldose reductase inhibitor on cataract formation in dogs fed a diet high in galactose," AJVR, vol. 67, No. 10, Oct. 2006,pp. 1783-1787. Cusick et al., "Effects of Aldose Reductase Inhibitors and Galactose Withdrawal on Fluorescein Angiographic Lesions in Galactose-Fed Dogs," Archives of Ophthalmology, vol. 121, Feb. 2007, pp. 1745-1751.

* cited by examiner

*Primary Examiner* — Karlheinz R Skowronek
*Assistant Examiner* — Sean Basquill
(74) *Attorney, Agent, or Firm* — Richard C. Litman

(57) ABSTRACT

The topical treatment of cataracts in dogs is a composition having an aldose reductase inhibitor (ARI) in a topical carrier. The ARI is preferably 2R,4S-6-fluoro-2-methyl-spiro[chroman-4,4'-imidazolidine]-2',5'-dione, referred to as 2R-methyl sorbinil, having the structure:

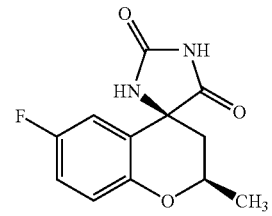

The topical carrier is formed from EDTA and deionized water containing about 2.5% carbomer, 1.5% glycerin, 0.02% EDTA and 0.1% benzalkonium chloride mixed to form a uniform emulsion. The concentration of the ARI in the topical carrier is preferably about 5-6%. The treatment includes administering to a dog an effective amount of the composition for preventing the formation of cataracts, reversing the formation of cataracts, and for treating diabetic retinopathy and pathological conditions resulting from diabetes affecting the cornea, iris, ciliary bodies, etc. The composition is preferably administered in the form of about two to four eye drops daily.

14 Claims, 11 Drawing Sheets

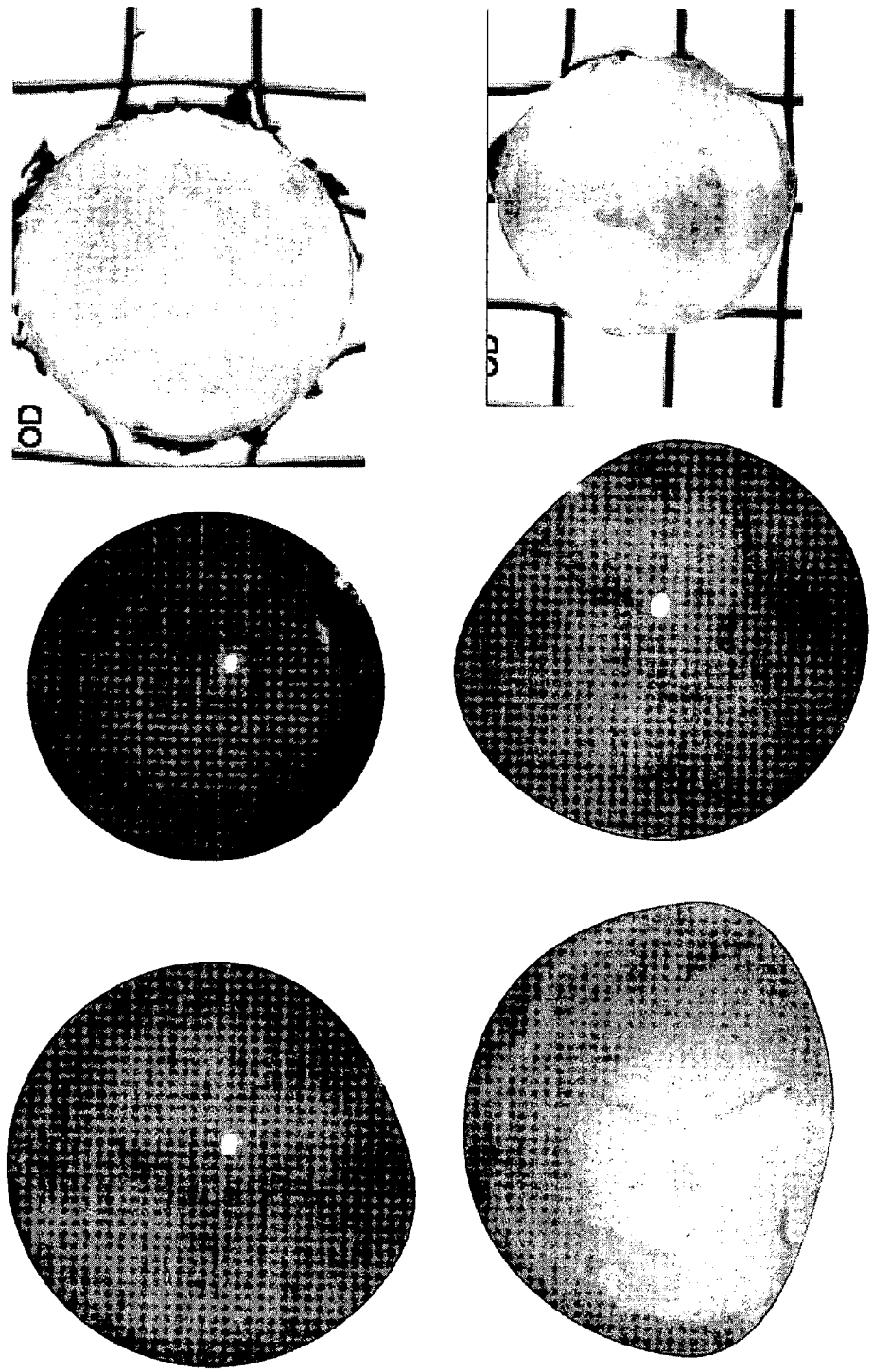

TOPICAL TREATMENT OF CATARACTS IN DOGS

CROSS-REFERENCE TO RELATED APPLICATION

This application claims the benefit of U.S. Provisional Patent Application Ser. No. 60/838,874, filed Aug. 21, 2006.

BACKGROUND OF THE INVENTION

1. Field of the Invention

The present invention relates to a method and composition for the topical treatment of cataracts and other complications of diabetes in dogs, and to a method for preparing the composition.

2. Description of the Related Art

In the United States, companion pets number over 62 million dogs and 71 million cats. According to the American Veterinary Medical Association (AVMA), these dogs and cats are living longer due to better nutrition and preventive veterinary care. With over 40% of this population being at least seven years old, more pets are being diagnosed with diabetes mellitus (DM). Although DM occurs at any age, it most frequently is diagnosed in dogs and cats between the ages seven and nine. In 1996, the prevalence of DM in dogs and cats was reported to range between 0.2-1%, i.e., approximately 1 in every 200 dogs and cats was diabetic. A number of complications result from diabetes mellitus, including the formation of cataracts; diabetic retinopathy; corneal lesions, erosion, wound healing complications, epithelial barrier changes, and other corneal pathology; changes in the iris (delay in dilation, fibrous tissue formation, altered vessel permeability, etc.); morphological changes in the ciliary bodies; and other diabetic changes.

Investigations have shown that many of the complications of diabetes result, at least in part, from abnormalities in glucose metabolism through the polyol pathway.

Normally the bulk of intracellular glucose is metabolized to provide energy by phosphorylation of glucose, which is catalyzed by hexokinase to form glucose-6-phosphate, which is further metabolized to useful energy by entry into the Krebs cycle. In the diabetic patient, however, insufficient hexokinase is available to metabolize all of the intracellular glucose.

In many tissues of the body, including lens tissue in the eye, an alternative path is available to metabolize glucose. The enzyme aldose reductase (AR) catalyzes the reduction of glucose to sorbitol with hydrogen supplied by NADPH. Sorbitol is then oxidized to fructose by sorbitol dehydrogenase, the hydrogen being accepted by $NAD^+$. However, in the hyperglycemic patient, although sufficient aldose reductase is available to reduce glucose to sorbitol, there is not sufficient sorbitol dehydrogenase to oxidize the sorbitol to fructose.

This leads to an accumulation of sorbitol in the tissues. Sorbitol does not readily diffuse through the tissues and cellular membranes due to its polarity. It is hypothesized that the accumulation of sorbitol produces a hyperosmotic condition, with resulting fluid accumulation in the cells, altering membrane permeability with the development of the pathological conditions noted above. Consequently, considerable attention has focused on the development of aldose reductase inhibitors (ARIs).

In order to investigate the specific role of AR, researchers have taken advantage of the broad substrate specificity of AR through the use of galactose-fed animals. Experimentally, galactose-induced tissue changes occur faster and progress to a more severe state than glucose-induced changes. This is because (1) intracellular galactose is more rapidly reduced to galactitol by AR than glucose is reduced to sorbitol and (2) higher intracellular levels of polyol are achieved with galactitol, since it is not further metabolized by sorbitol dehydrogenase. While not diabetic, the galactose-fed animal has become a specific model for investigating the role of AR in diabetes-like complications. If AR is involved in the mechanism(s) initiating the diabetic lesion, then the biochemical and pharmacological results obtained with ARIs in the galactose-fed animals should be complementary to that in diabetic animals.

According to one path of ARI development, it was found that certain flavonoids (rutin and hesperidin) having a chroman or chromone ring structure, such as that shown in I below, exhibit ARI activity.

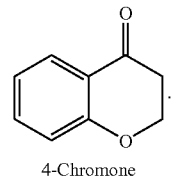

4-Chromone

I

It was then found than the chroman ring structure in combination with a hydantoin structure, shown in II below, produces a spirohydantoin having a greater ARI effect.

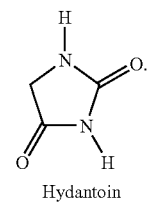

Hydantoin

II

Thus, in U.S. Pat. No. 4,130,714, Sarges describes the synthesis of d-6-fluoro-spiro[chroman-4,4'-imidazolidine]-2',5'-dione, commonly known as sorbinil, shown in III below, and its oral or parenteral administration for the treatment of diabetic complications.

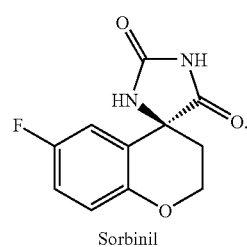

Sorbinil

III

In U.S. Pat. No. 4,540,704, issued Sep. 10, 1985, Ueda et al. describe the preparation of various spirohydantoin compounds, including the compound 6-fluoro-2-methyl-spiro-[chroman-4,4'-imidazolidine]-2',5'-dione, commonly known as methyl sorbinil or 2-methyl sorbinil, shown in IV below.

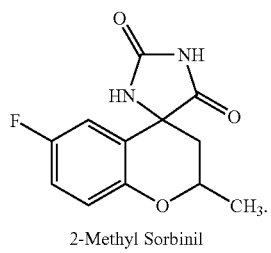

2-Methyl Sorbinil

IV

The '704 patent recites various experiments on galactosemic rats to show that the compounds described therein are effective in the treatment and prevention of diabetic cataracts, diabetic neuropathy, diabetic nephritis, and various arteriosclerotic blood vessel lesions resulting from diabetes mellitus. The '704 patent notes particularly that 2-methyl sorbinil is 2-10 times more effective than sorbinil in preventing the accumulation of sorbitol, and is also more effective in inhibiting aldose reductase. The patent recites that the compounds may be administered orally, parenterally, or topically, but does not list a formulation of eye drops, a cream, or an ophthalmic gel. It will be noted that 2-methyl sorbinil has two chiral centers, at the 2 position and at 4,4', and that the synthesis described in the '704 patent results in a mixture of stereoisomers.

Various studies have shown that diabetic cats are not prone to develop sugar cataracts, since the levels of AR in the cat lens is not as high as in dogs of the same age. Diabetic dogs, however, are prone to develop bilateral cataracts, and research as shown that this is related to AR levels in the lens. Research studies have also shown that the oral administration of aldose reductase inhibitors to dogs have been effective in the prevention of cataracts resulting from diabetes, as well as in the treatment of diabetic retinopathy, corneal lesions, and other complications of diabetes mellitus.

Nevertheless, the oral administration of aldose reductase inhibitors has several shortcomings. The dosage of ARIs administered orally is rather high (about four times per day), and must be maintained over a long period of time. Oral administration requires processing by the liver, and may compromise the dog's liver function. Moreover, no studies have yet shown reversal of the formation of cataracts in dogs from the oral administration of aldose reductase inhibitors.

No topical formulation for administering an ARI directly into the dog's eyes is currently known. Conventional topical formulations for ARIs are not effective for use on dogs, since such formulations are generally aqueous solutions, and tear flow in dogs is generally greater than in humans, so that it is not possible to maintain therapeutic levels of an ARI, since such formulations are washed out by tear formation.

A topical formulation for the administration of an ARI directly into a dog's eyes would be desirable for reduction of dosage and frequency of administration, quicker absorption into the system, and avoiding liver metabolism of the ARI. Moreover, a method of preparing such a topical formulation that includes an improved synthesis of 2R-methyl sorbinil having fewer steps and producing greater yield than conventional methods is desired. Thus, a topical treatment of cataracts in dogs solving the aforementioned problems is desired.

SUMMARY OF THE INVENTION

The topical treatment of cataracts in dogs is a composition having an aldose reductase inhibitor (ARI) in a topical carrier. The ARI is preferably 2R,4S-6-fluoro-2-methyl-spiro[chroman-4,4'-imidazolidine]-2',5'-dione, referred to as 2R-methyl sorbinil, having the following structure:

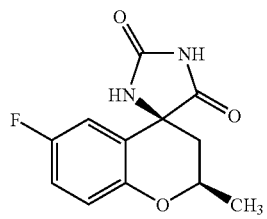

The topical carrier is formed from EDTA and deionized water containing about 2.5% carbomer, 1.5% glycerin, 0.02% EDTA and 0.1% benzalkonium chloride mixed to form a uniform gel-like emulsion. The concentration of the ARI in the topical carrier is preferably about 5-6%. The treatment includes administering to a dog an effective amount of the composition for preventing the formation of cataracts, reversing the formation of cataracts, and for treating diabetic retinopathy and pathological conditions resulting from diabetes affecting the cornea, iris, ciliary bodies, etc. The composition is preferably administered in the form of about two to four eye drops of the emulsion daily.

Preparation of the composition includes an improved stereospecific synthesis of 2R-methyl sorbinil. The synthesis described herein reduces the number of stages in conventional methods by replacing resolution of an intermediate using chymotrypsin with selective recrystallization of the intermediate, which simplifies the synthesis and also increases the yield of the desired stereoisomer.

These and other features of the present invention will become readily apparent upon further review of the following specification and drawings.

BRIEF DESCRIPTION OF THE DRAWINGS

FIG. 3A shows photographs of the appearance of lenses in two dogs (the top and bottom rows respectively) after fifteen weeks of galactose feeding (first column), after nine weeks of administration of carrier only without an ARI, and the lenses placed over a grid after dissection at twenty-six weeks.

Similar reference characters denote corresponding features consistently throughout the attached drawings.

DETAILED DESCRIPTION OF THE PREFERRED EMBODIMENTS

Figure 1:
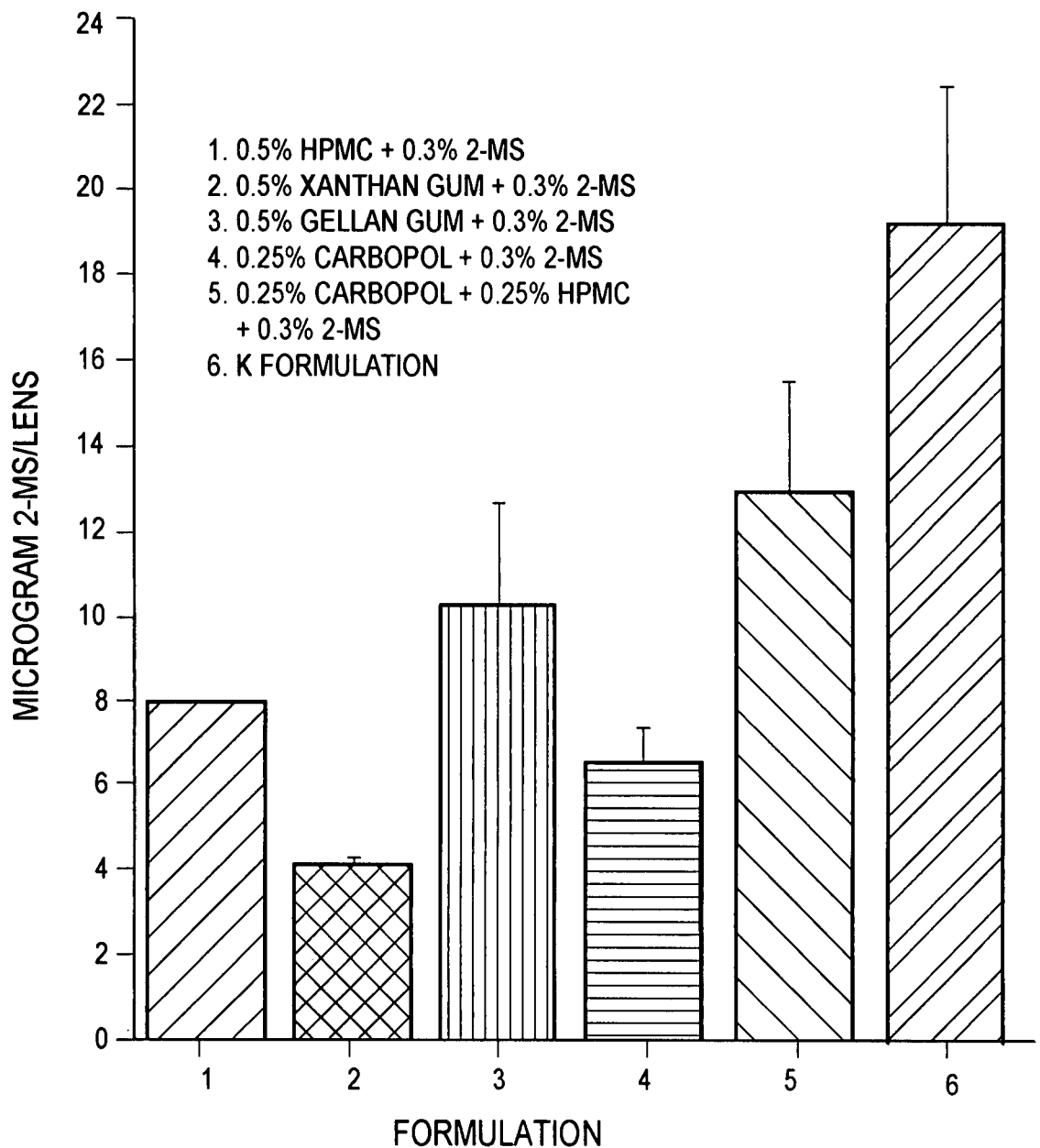
FIG. 1 is a chart showing the delivery of 2R-methyl sorbinil to the lens in galactose-fed rats for various topical carriers for comparison to the topical treatment of cataracts in dogs according to the present invention.

The present invention relates to a topical treatment of cataracts in dogs. The present invention particularly extends to a composition that includes an aldose reductase inhibitor (ARI) in a topical carrier that is specifically designed for administration to dogs. The present invention also extends to a method of treating diabetic complications in a dog, including cataracts, diabetic retinopathy, and diabetic complications affecting the cornea, the iris, ciliary bodies, and tear formation, etc., by administering an effective amount of the topical treatment to the dog. The present invention further extends to an improved synthesis of a particular ARI, viz., 2R,4S-6-fluoro-2-methyl-spiro[chroman-4,4'-imidazolidine]-2',5'-dione, which is believed to be the more effective stereoisomer of 2-methyl sorbinil in inhibiting aldose reductase.

The topical treatment of the present invention is a composition that includes an ARI in a topical carrier. Aldose reductase inhibitors have been shown to be effective in diabetic or galactose-fed dogs and rats for the prevention of sugar cataracts, the treatment of diabetic retinopathy, and other complications of diabetes affecting the cornea, the iris, ciliary bodies, tear formation, etc., when the ARI is administered orally or parenterally. There is currently no topical treatment for the prevention of cataracts and other such complications of diabetes that is effective in dogs.

Dogs have a tendency to produce a greater quantity of tears than humans. A conventional topical carrier for an ARI is a substantially aqueous solution. For example, a representative eye drop formulation might include only the ARI in water, sodium chloride, and benzalkonium chloride. Such a carrier would not work in dogs, since the ARI would be washed out of the dog's eyes by tears before a therapeutic level of ARI could be achieved. A more viscous topical carrier is required to allow for transport of the ARI through the cell membranes.

In the present invention, any aldose reductase inhibitor may be used with the topical carrier described herein. However, a preferred ARI is 6-fluoro-2-methyl-spiro[chroman-4,4'-imidazolidine]-2',5'-dione, and more preferably the stereoisomer 2R,4S-6-fluoro-2-methyl-spiro[chroman-4,4'-imidazolidine]-2',5'dione, also referred to herein as 2R-methyl sorbinil, or simply 2R-MS.

Topical administration of the ARI 2R,4S-6-fluoro-2-methyl-spiro[chroman-4,4'-imidazolidine]-2',5'-dione (2-MS) is the preferred method for preventing cataracts and ocular complications in diabetic dogs and cats. As a result of the short, 3 hr systemic half-life of 2-MS in dogs and subsequent studies conducted in galactose-fed dogs, it is estimated that, at minimum, a multiple 4-times/day oral dose is required for efficacy. Topical application permits a lower dosage and a lower frequency of administration. Topical application will also minimize the tendency of diabetic dogs to have their liver functions compromised because topical administration will bypass first pass liver metabolism. The topical treatment of the present invention will not only arrest the progression of sugar cataracts, but also reduces the density of early cortical cataracts. This indicates that the topical treatment may serve as a prophylactic treatment against the formation of cataracts and, subsequently, the need for cataract surgery in the growing market of diabetic dogs. Moreover, the restoration of functional vision in the dogs with early cortical sugar cataracts suggests that the need for surgery in select dogs with diabetes mellitus and early cataracts may also be reduced. The topical treatment should also delay the formation of other ocular diabetes associated complications associated with aldose reductase, as summarized above.

Example 1

Synthesis of 2R,4S-6-fluoro-2-methyl-spiro[chroman-4,4'-imidazoline]-2',5'-dione As compared to conventional methods for synthesizing this stereoisomer of 2-methyl sorbinil, the overall synthesis of the present invention reduces the number of steps from eleven to eight steps and the overall yield is increased from 3.1% to 15%. In this synthesis, resolution using chymotrypsin, as exemplified in U.S. Pat. No. 4,841,079, issued Jun. 20, 1989 to F. J. Urban, for example, has been replaced by a selective crystallization step. The final product was tested and found identical to 2-MS previously obtained from Eisai Co., Ltd. of Tokyo, Japan (assignee of the '704 patent to Ueda et al.) by NMR, MS, melting point, HPLC elution, and biological activity.

All reactions and compound purities were monitored by reverse phase HPLC using a 250×4.6 mm $C_{18}$ Luna column (5µ100 Å) with a mobile phase of 75:25 methanol:water at a flow rate of 0.9 mL/min, and detection at 220, 254 and 280 nm. This HPLC procedure was used for all products. The steps in the synthesis are as follows.

(R)-Ethyl-2-(4-Fluorophenoxy)propionate (3). Under argon, 100 g (0.892 mol) of 4-fluorophenol (2) was combined with 105.2 g (0.892 mol) of (S)-ethyl lactate and 233.8 g (0.892 mol) of triphenylphosphine in 1200 mL of tetrahydrofuran (THF). The reaction mixture was cooled to −5° C., and 180.4 g (0.892 mol) of diisopropylazodicarboxylate (DIAD) in 500 ml of THF was dropwise added. The ice bath was removed, and stirring was continued at room temperature for 18-22 hr. THF was then evaporated in vacuo, and 1400 mL of hexane-ether (80:20) was added to the residue, and the remaining solid was removed by filtration. The filtrate was then washed with 2×600 mL of 1N NaOH, followed by 2×600 mL of water and 600 mL of brine. The washed filtrate was then dried over $MgSO_4$, filtered and then evaporated to give 185 g of (R)-ethyl-2-(4-fluorophenoxy)-propionate, 7, as a light yellow oil in 98% yield, Bp 80° C. at 0.7 mm Hg. The reaction is shown as follows:

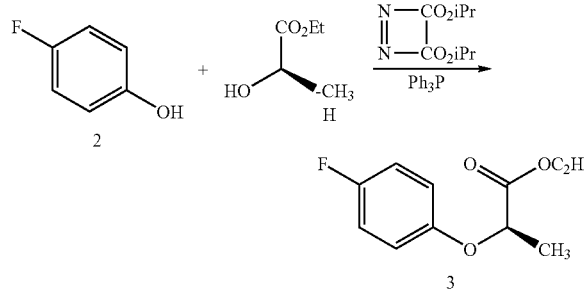

(R)-2-(4-Fluorophenoxy)propan-1-ol (4). Under argon (Ar), lithium aluminum hydride (LiAlH$_4$) (35.21 g, 0.98 mol) in 2.2 L of dry ether was placed in a 5-liter three-necked flask equipped with reflux condenser, dropping funnel, and mechanical stirrer under dry Ar. The mixture was cooled to 0-5° C., and a solution of 3 (185 g, 0.87 mol) in 1 L of ether was added dropwise. After the addition, the stirred mixture was allowed to slowly come to room temperature and stirred for 16-18 hr until no starting material could be detected by HPLC. The mixture was again cooled in an ice bath and excess hydride was carefully decomposed by addition of 6N HCl (750 mL). Stirring was continued overnight until the solution became a clear, light yellow color. The reaction mixture was extracted with 2×500 mL ethyl ether, and the combined ether layers were then washed with 2×700 mL of water and 500 mL of brine. The ether was evaporated, and the residue was dissolved in 700 mL of CH$_2$Cl$_2$ and dried over MgSO$_4$. After filtration, the organic solvent was removed in vacuo to yield 159 g of a yellow oil in 95% yield. HPLC retention time 4.1 min, Bp 70° C. at 0.7 mm Hg. The reaction is shown as follows:

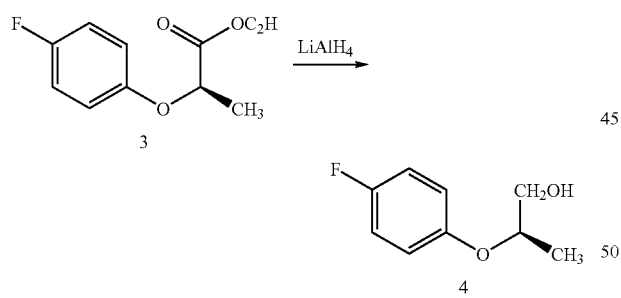

(R)-1-Bromo-(4-fluorophenoxy)propane (5). 149 g (0.875 mol) of 4 and 97.2 g (0.875 mol) of triphenylphosphine (TPP) dissolved in 300 mL of dimethylformamide (DMF) maintained under argon at 22° C., to which was added dropwise 159.8 g (0.875 mol) of bromine. The mixture was stirred for 24 hrs. 2.5 L of ethyl acetate was then added to the reaction mixture and, after stirring an additional one hour, the organic layer was washed with 4×800 mL of water, 1 L saturated NaHCO$_3$, and 700 mL brine. The organic layer was dried over MgSO$_4$, filtered and concentrated in vacuo. The residue was dissolved in 1.5 L of hexane, stirred at 10° C. 2 hrs, and filtered. High vacuum distillation gave the product 5 in 74% yield (151 g). HPLC retention time 9.1 min, Bp 72-74° C. at 0.25 mm Hg. The reaction is shown as follows:

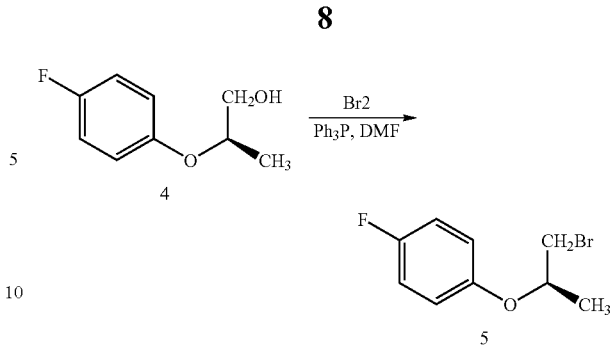

(R,S)—N-Benzoyl-[2-((2R)-1-bromopropanoxy)-5-fluorophenyl]glycine (6). α-Hydroxyhippuric acid (156 g 0.86 mol) was added to a stirred solution of 5 (200.4 g, 0.86 mol) in cold methyl sulfonic acid (629 mL), and the reaction mixture was maintained under 20° C. with stirring for 30 min. Stirring was continued until the product 5 disappeared by HPLC (48 hr). The thick reaction mixture was added with stirring to 2.5 L of ice water. The product precipitated as a yellow solid, which was filtered, washed with water, and air dried to a constant weight (321 g, 92% yield). The solid product, (R,S)—N-benzoyl-[2-((2R)-1-bromopropanoxy)-5-fluorophenyl]-glycine, 6, was used without further purification for the next reaction. HPLC retention time 5.16 min. The reaction is shown as follows:

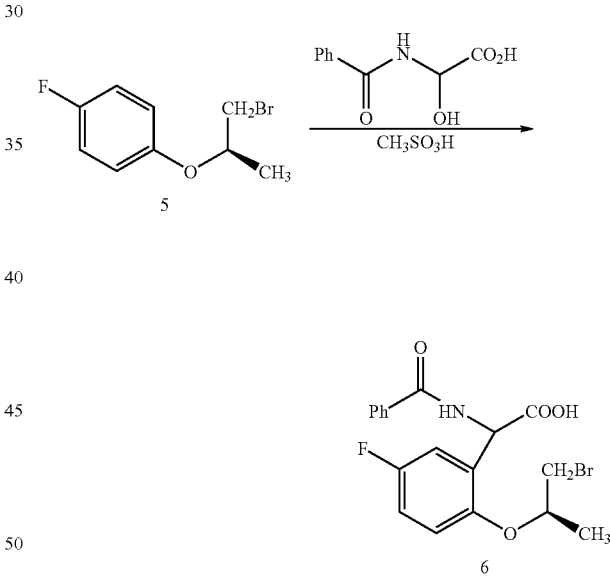

6-Fluoro-2(R)-methylspiro[chroman-4,4'-phenylaxazolidine-5'-one] (7). Compound 6 (292 g, 0.711 mol) was suspended in 1170 mL acetone with 216.4 g (1.56 mol) of anhydrous K$_2$CO$_3$ and cooled with an ice bath. Acetic anhydride (108.9 g, 0.1.067 mol) was then added, and the mixture was stirred at room temperature for 24 hrs. The reaction mixture was filtered through Celite #521, and the filter was washed with 2×200 mL of acetone. The filtrate and acetone wash were combined and concentrated in vacuo to give brown semi-solid material. The material was dissolved in 1.2 L of ether, and following 30 min of sting at 10° C., the solution was again filtered through Celite. Evaporation of ether in vacuo gave 176 g (79%) of brown solid (7). The reaction is shown as follows:

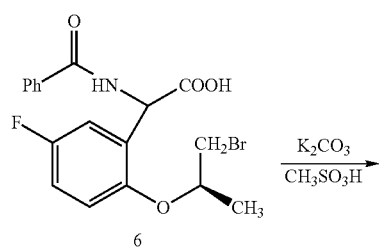

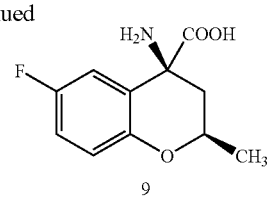

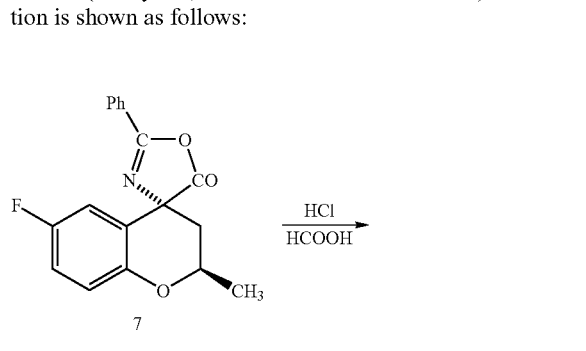

4(RS)-Amino-6-fluoro-2(R)-methylchroman-4-carboxylic acid (8). 176 g of 7 in 500 mL of formic acid and 690 mL of con. HCl was refluxed 12 hours, then cooled and concentrated in vacuo to give a dark brown semi-solid mass. This was dissolved in 1.2 L of water and washed with 700 ml of ethyl ether. The pH of the aqueous layer was adjusted to 5 with 1.0 N NaOH and then evaporated in vacuo to give 124 g of white solid 8. (92% yield, HPLC retention time 3.0 min). The reaction is shown as follows:

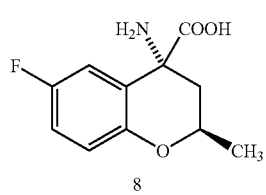

Repetitive recrystallization of 8 from hot water gave the desired 4(S)-Amino-6-fluoro-2(R)-methylchroman-4-carboxylic acid (9) in 33% yield (40.9 g) mp 228-229° C. with an optical purity of over 94%. The reaction is shown as follows:

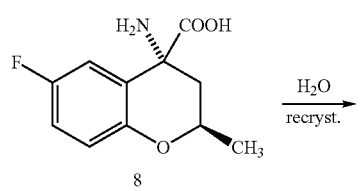

2R,4S-6-fluoro-2-methyl-spiro[chroman-4,4'-imidazolidine]-2'-5'-dione (1). The acid 9 (90 g, 0.40 mol), dissolved in 1 L water, was stirred at room temperature with 52 g (1.0 mol) sodium cyanate and stirred at room temperature. The pH value was adjusted to 7.00 with 6.0 M HCl until stabilized at pH 7.00. After 24 hrs, the pH was adjusted to 2.00 to obtain a white solid, which was dissolved in 80 mL of glacial acetic acid and refluxed for 5 hrs. After the addition of 1 L of water, a crystalline white solid was obtained. This was recrystallized in 10% aqueous methanol to yield 34 g (37%) of product 1, mp 235-236° C. HPLC retention time 3.47 min. $^1$H-NMR DMSO-$d_6$, σ, ppm): 1.31 d (2H, J=6.3 Hz); 1.81 t (1H, J=11.8 Hz); 2.28 d (1H, J=13.6 Hz); 4.75 m (1H); 6.90 m (2H); 7.08 m (1H); 8.35 s (IH, NH), 10.93 s (1H, NH) $^{13}$C-NMR C-2: 79.8; C-3: 37.7; C-4: 60.5; C-5: 121.9 ($^3J_{C\text{-}F}$=6.7 Hz); C-6: 112.8 ($^2J_{C\text{-}F}$=23.5 Hz); C-7: 157.5 ($^1J_{C\text{-}F}$+70.1 Hz); C-8: 117.5 ($^2J_{C\text{-}F}$=23.1 Hz); C-9: 119.2 ($^3J_{C\text{-}F}$=7.6 Hz); C-10: 152.3 ($^4J_{C\text{-}F}$=1.9 Hz); C-11: 177.4; C-12: 157.3; C-13: 21.4. The reaction is shown as follows:

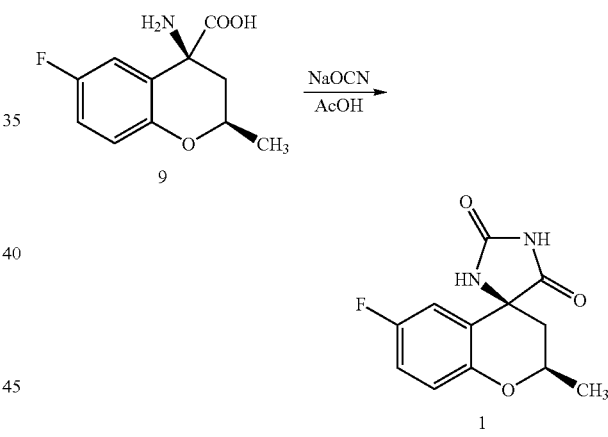

Alternatively, 4(S)-Amino-6-fluoro-2(R)-methylchroman-4-carboxylic acid (9) can be obtained from (R)-6-fluoro-2,3-dihydro-2-methylchromen-4-one (12) through an enantioselective Strecker synthesis. Compound 12 is obtained from (R)-1-bromo-(4-fluorophenoxy)propane (5) and converted to 4(S)-amino-6-fluoro-2(R)-methylchroman-4-carboxylic acid (9). The process is described according to the following steps.

(R)-3-(4-fluorophenoxy)butanenitrile (10). To a stirred solution of the bromide 5 (12.82 g, 55 mmol) dissolved in DMSO (60 mL) was added dry KCN (1.95 g, 30 mmol), and the reaction mixture was stirred at 40° C. for 3.5 hours until the KCN powder had disappeared. The reaction was quenched with saturated aqueous NH$_4$Cl solution (150 mL). After extraction with ethyl acetate, the combined organic layers were washed with 1N NaOH, water, and brine. After drying over Na$_2$SO$_4$, the organic layer was filtered and ethyl acetate was evaporated in vacuo. The residue was then vacuum distilled at 130-135° C. at 1.0 mm Hg to give 5.35 g (54.6%) of product as a colorless oil. Further distillation yielded 5.8 g (45.2%) of recovered bromide 5. $^1$H NMR (CDCl$_3$) δ 7.01-6.98 (m, 2H), 6.90-6.87 (m, 2H), 4.55-4.52 (m, 1H), 2.68 (d, J=5.5 Hz, 2H), 1.48 (d, J=6.5 Hz, 3H). EI-MS (m/z) 179 (M$^+$+1). The reaction is shown as follows.

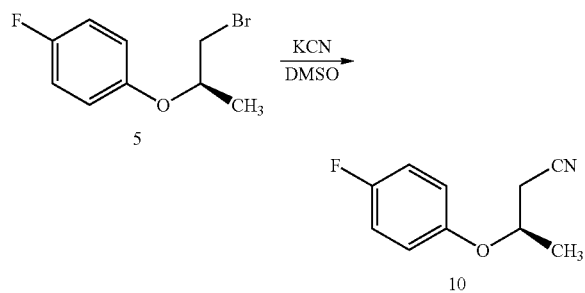

(R)-3-(4-fluorophenoxy)butanoic acid (11). A mixture of the nitrile 10 (1.14 g, 6.4 mmol), concentrated HCl (3.6 mL) and 99% HCOOH (3.0 mL) was heated to 90° C. for 3.5 hours. After slight cooling, ice cold water (5.0 mL) was poured onto the reaction mixture, and the water layer was extracted with ethyl acetate. The combined organic layers were dried over Na$_2$SO$_4$, filtered and evaporated in vacuo. The resulting residue was dissolved in 1N NaOH (8 mL), stirred at room temperature for 30 min., and then extracted with ethyl acetate. The water layer was then acidified to pH 1 with 6N HCl, extracted with ethyl acetate and dried over Na$_2$SO$_4$. After filtration and evaporation of the ethyl acetate solvent, 1.04 g (82%) of pale yellow oil was obtained. $^1$H NMR (CDCl$_3$) δ 6.98-6.93 (m, 2H), 6.90-6.86 (m, 2H), 4.73-4.69 (m, 1H), 2.81 (dd, J=7.0, 16.0 Hz, 1H), 2.58 (dd, J=6.0, 16.0 Hz, 1H), 1.35 (d, J=6.5 Hz, 3H). The reaction is shown as follows:

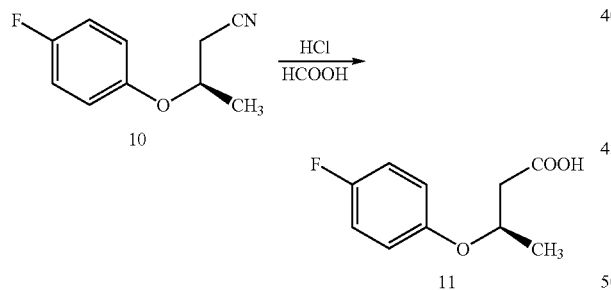

(R) 6-fluoro-2,3-dihydro-2-methylchromen-4-one (12). To a solution of the acid 11 (1.04 g, 5.25 mmol) in CH$_2$Cl$_2$ (20 mL) were slowly added trifluoroacetic acid (7 mL) and trifluoroacetic anhydride (7 mL), and the mixture was stirred for three hours at room temperature. The reaction mixture was then poured onto ice and the CH$_2$Cl$_2$ layer was separated. The water layer was extracted with CH$_2$Cl$_2$, and the combined organic layers were washed with water, saturated aqueous NaHCO$_3$ and brine, and dried over Na$_2$SO$_4$. The chloroform layer was then filtered and evaporated in vacuo to give 770 mg (82%) of a white solid 12, m.p. 72-75° C., $^1$H NMR (CDCl$_3$) δ 7.54-7.52 (m, 1H), 7.26-7.17 (m, 1H), 6.99-6.94 (m, 1H), 4.61-4.54 (m, 1H), 2.68 (dd, J=6.0, 11.0 Hz, 2H), 1.52 (d, J=6.5 Hz, 3H). EI-MS (m/z) 180 (M$^+$). The reaction is shown as follows:

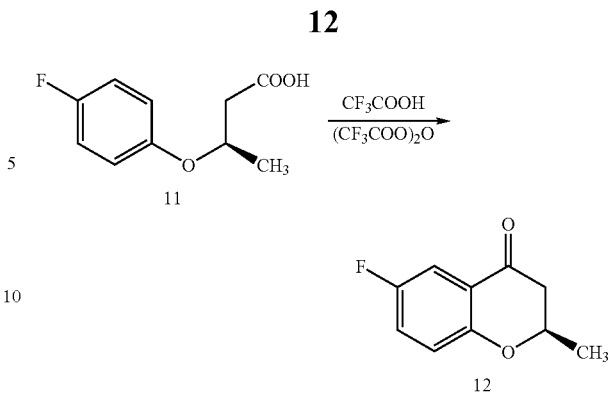

(R) 6-fluoro-2,3-dihydro-2-methylchromen-4-oxime (13). To a suspension of the ketone 12 (2.79 g, 15.5 mmol) was added a solution of hydroxylamine hydrochloride (2.09 g, 30 mmol) and K$_2$CO$_3$ (1.2 g, 8.75 mmol) in 18 mL of H$_2$O. The reaction mixture was refluxed for four hours. After cooling to room temperature, the solution was removed under vacuum, and the residual solid was triturated with ice water. The crude product was recrystallized from EtOH to give 3.2 g (84%) of the white solid oxime 13, m.p. 102-105° C., $^1$H NMR (CDCl$_3$) δ 7.58 (br s, 1H), 7.48 (dd, J=3.0, 9.5 Hz, 1H), 6.97 (ddd, J=3.0, 9.0, 8.0 Hz, 1H), 6.85 (dd, J=4.5, 9.0 Hz, 1H), 4.21-4.15 (m, 1H), 3.28 (dd, J=3.0, 17.0 Hz, 1H), 2.37 (dd, J=12.0, 17.0 Hz, 1H), 1.47 (d, J=6.5 Hz, 3H). EI-MS (m/z) 195 (M$^+$). The reaction is shown as follows:

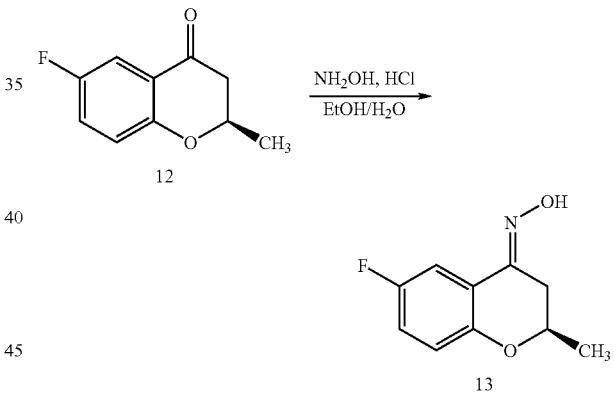

N—((R)-2-methyl-6-fluoro-2,3-dihydro-4H-1-benzopyran-4-ylidene)-P,P-diphenylphosphinic amide (14). To a solution of oxime 13 (2.78 g, 14.26 mmol) in hexane (100 mL) and CH$_2$Cl$_2$ (100 mL) was added NEt$_3$ (2.3 mL, 17.5 mmol). The reaction mixture was cooled at −45° C. for 5 min and a solution of ClPPh$_2$ (3 mL, 17.1 mmol) in CH$_2$Cl$_2$ (10 mL) was then dropwise added over 45 min while the reaction mixture was maintained at −45° C. The reaction mixture was stirred an additional hour at −45° C. and then returned to room temperature. Stirring was continued at room temperature for an additional hour. The solvent was removed at 15° C. and the remaining yellow slurry was dissolved in CH$_2$Cl$_2$. The CH$_2$Cl$_2$ layer was washed with water and brine and dried over Na$_2$SO$_4$. After filtration and evaporation in vacuo, the residue was purified by silica gel column chromatography using 1:1 ethyl acetate:hexane as eluent to yield 4.63 g (85.7%) of white solid product, which, upon recrystallization from toluene-hexane, gave 3.27 g (60.5%) of the phosphinic amide 14 as white needles, m.p. 211-215° C. $^1$H NMR (CDCl$_3$) δ 8.03-

8.00 (m, 2H), 7.99-7.85 (m, 3H), 7.50-7.41 (m, 1H), 7.19-6.89 (m, 1H), 4.39 (ddq, J=2.5, 13.0, 6.0 Hz, 1H), 4.01 (ddd, J=2.5, 2.5, 17.5 Hz, 1H), 2.77 (ddd, J=3.0, 13.0, 17.5 Hz, 1H), 1.44 (d, J=6.0 Hz, 3H); $^{13}$C NMR (CDCl$_3$) δ 174.9 (dd, J=2.5, 6.8 Hz), 157.0 (d, J=239.0 Hz), 156.9, 134.3 (d, J=130.0 Hz), 131.6 (d, J=9.0 Hz), 131.3 (d, J=9.0 Hz), 131.5 (d, J=2.9 Hz), (d, J=12.9 Hz), 128.4 (d, J=12.4 Hz), 122.3 (dd, J=6.8, 24.5 Hz), 122.7 (d, J=24.4 Hz), 119.6 (d, J=6.1 Hz), 111.8 (d, J=23.4 Hz), 73.4, 40.0 (d, J=11.9 Hz), 20.6; EI-MS (m/z) 379 (M$^+$). The reaction is shown as follows:

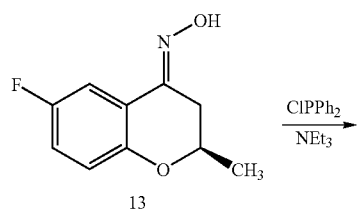

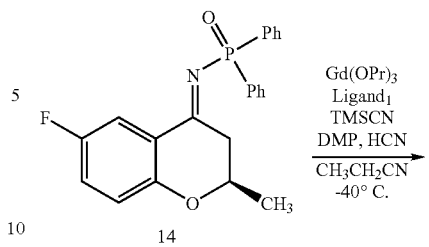

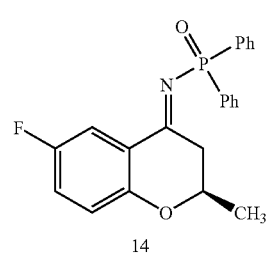

N—((R)-2-methyl-(S)-4-cyano-6-fluoro-3,4-dihydro-2H-7-benzpyran-4-yl)-P,P-diphenyl-phosphinic acid-1-benzopyran (15). An enantioselective Strecker reaction was conducted under argon by adding Gd(OiPr)$_3$ (0.2 M) dissolved in 0.125 mL of THF to 1,5-anhydro-2,6-dideoxy-3-O-(4,5-difluoro-2-hydroxyphenyl)-6-(diphenylphosphinyl)-D-arabino-hexitol ligand (23 mg, 0.5 mL) dissolved in 0.5 mL THF at 0° C. The mixture was stirred for 40 min at 45° C., the solvent was then evaporated, and the resulting pre-catalyst was dried under high vacuum for 2 hours. The ketoimine 14 (80 mg, 0.21 mmol) was then added as a solid, followed by propionitrile (0.125 mL) at −40° C. After 20 min, the reaction was started by addition of 2,6-dimethylphenol (30 mg, 0.25 mmol) in propionitrile (0.1 mL), and the reaction was maintained at −40° C. with stirring for 6 hours. The reaction temperature was then allowed to gradually warm to room temperature for 60 hours, and 100 mg of silica gel was added to the reaction. The reaction mixture was then evaporated until HCN generation ceased. The silica gel was filtrated, washed with MeOH/CHCl$_3$ (1/9) and the combined filtrate was evaporated in vacuo. The remaining residue was purified by silica gel column chromatography using 100:1 CHCl$_3$:MeOH as eluent to yield 77 mg (90%) of white solid as an optical pure product 15, m.p. 160-162° C. $^1$H NMR (CDCl$_3$) δ 8.04 (dd, J=2.5, 7.5 Hz, 1H), 7.84 (dd, J=7.5, 12.0 Hz, 1H), 7.61-7.41 (m, 7H), 6.97 (ddd, J=3.0, 7.5, 9.0 Hz, 1H), 6.80 (dd, J=4.5, 9.0 Hz, 1H), 4.38-4.33 (m, 1H), 3.57 (d, J=5.0 Hz, 1H), 3.01 (d, J=14.0 Hz, 1H), 2.29 (t, J=13.0, 1H), 1.42 (d, J=6.0 Hz, 3H); ESI-MS (m/z) 402 ([M+Na]$^+$). The reaction is shown as follows:

4-(S)-Amino-6-fluoro-2(R)-methylchroman-4-carboxylic acid (9). Product 15 (170 mg, 0.42 mmol) was treated with 8 mL of concentrated HCl for 10 hr at 90° C. After cooling to room temperature, excess acid was removed in vacuo, and 5 mL H$_2$O was added to the residue. The resulting suspension was extracted with ethyl acetate; all of the solid had dissolved. The water layer was then adjusted to a pH of 5 with 1.0 N NaOH, and then evaporated in vacuo to give a white solid, which was recrystallized from water to give 49 mg (52%) of white powder 9, m.p. 153-156° C., $^1$H NMR (DMSO-d$_6$) δ 7.11 (ddd, J=2.9, 8.3, 9.3 Hz, 1H), 7.07 (dd, J=2.9, 8.3 Hz, 1H), 6.93 (dd, J=4.9, 9.3 Hz, 1H), 4.64-4.62 (m, 1H), 2.46 (d, J=14.2 Hz, 1H), 1.40 (d, J=6.4 Hz, 3H); ESI-MS (m/z) 226 ([M+H]$^+$). The reaction is shown as follows:

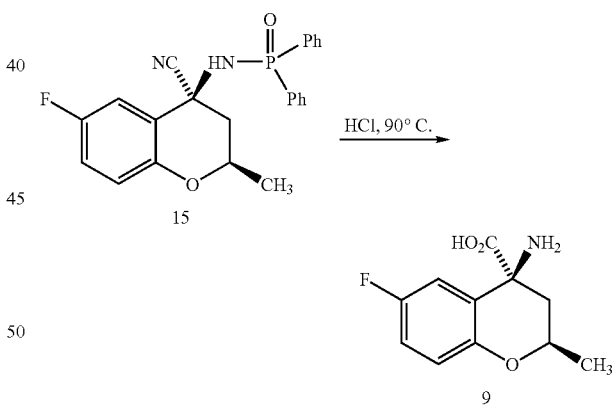

Topical ARI treatment requires adequate drug absorption through the cornea and conjunctiva. The cornea and conjunctiva are protected by tears and the eyelid, whose function is to provide nutrition and oxygen to the corneal surface; to lubricate; and to remove foreign matter, including ophthalmic solutions or suspensions, from the corneal and conjunctival surfaces. Tear flow in dogs is significantly higher than in humans Therefore, increased retention of the topical ARI formulation is required for adequate ocular uptake of the ARI to be achieved. The viscosity of ophthalmic solutions is often increased to prolong their retention on ocular surfaces and to increase the bioavailability of the drug.

Example 2

Testing of Topical Carriers

To maximize the topical administration of 2R-MS, vehicles or carriers of different viscosities comprised of polymers, gums, or viscosity enhancers were prepared. Formulations containing 3% of the AR inhibitor 2R-MS were prepared using the five different vehicles, which included 0.5% hydroxypropyl methylcellulose (HPMC); 0.5% xanthan gum; 0.5% gellan gum; 0.25% carbopol; and 0.25% carbopol (0.25% w/v)+0.25% HPMC. All were prepared in modified Sorensen's Phosphate Buffer, pH of 7.4. The drug and each vehicle were suspended directly in a sterile eye drop bottle by vortexing vigorously for at least one minute. The particle sizes of the suspension were subsequently reduced by sonication. All suspensions were vortexed prior to topical administration. An additional topical carbomer gel formulation consisting of 2.5% water soluble high molecular weight polymer of acrylic acid cross-linked with a polyether of sucrose was also developed. Carbomers are widely used in products for the treatment of dry eye. Crystalline 2R-MS was ground into a fine powder and mixed into an emulsion according to standard techniques. At room temperature, the 2R-MS is stable in the emulsion for a minimum of ten months.

The topical treatment of the present invention was prepared as follows. The vehicle (topical carrier) is prepared by combining EDTA with deionized water and, once mixed, dispersing a carbomer that is composed of a water soluble anionic high molecular weight polymer of acrylic acid cross-linked with a polyether of sucrose. After the resin has fully wetted, it is stirred at slow speed. Benzalkonium chloride preservative is then added to the gel, followed by glycerin mixed with Sorensen's Phosphate Buffer, pH of 7.4. The solution is then heated with mixing until all solids are dissolved. The final vehicle contains 2.5% carbomer, 1.5% glycerin, 0.02% EDTA and 0.01% benzalkonium chloride.

The vehicle is placed in a 60 mL sterile syringe, and sterile, finely ground 2R-MS powder is placed in a second 60 mL syringe connected to the first syringe through a 3-way stopcock. Vehicle is transferred back and forth between the two syringes until a uniform emulsion is formed. This emulsion is then transferred to sterile 20 mL ophthalmic tubes and sealed. The final gel contains 5% 2R-MS. Alternatively, the vehicle is mixed under sterile conditions with finely ground 2-MS powder using a commercial ointment mixer until the composition has a gel-like consistency. The final gel, which contains 5% 2-MS, is then transferred to sterile tubes.

These formulations were evaluated in young (50 g) Sprague Dawley rats according to protocol 03-048-06 approved by the University of Nebraska Medical Center (UNMC) IACUC. Each separate group, composed of six rats, was administered a topical formulation for seven days, with one drop per eye being administered two times/day at 8 AM and 4 PM. After seven days, each rat was euthanized and the eyes were enucleated and frozen. Because of the low lenticular levels of 2-MS, one lens from three separate rats within the same group were combined for each analysis. The lenses were homogenized with 2 ml of 48 mM NaF containing equal amounts of sorbinil as an internal standard. The homogenates were centrifuged, acidified to pH 1.5 by with HCl, and extracted with diethyl ether.

The ether layer was washed with 0.25 M phosphate buffer, pH 7. The ether layer was then evaporated with a stream of nitrogen gas and the residue was dissolved in 200 μL of methanol. The levels of 2R-MS and sorbinil in each sample were determined by reverse phase HPLC on a Waters System using a Phenomenex 5 μm C18 column (250×4 mm) with isocratic 55% aqueous methanol at a flow rate of 1.2 mL/min. Peaks were monitored with a variable wavelength detector at 220 nm. Standard curves with sorbinil and 2R-MS were constructed, and concentrations between 0-70 μg of 2R-MS were linear. Both compounds were readily separated with 2R-MS displaying a 1.5 minute slower retention time than its parent compound, sorbinil. Because of its structural similarity and faster retention time, sorbinil was used as an internal standard for the subsequent extraction procedures.

Each formulation was also evaluated for its ability to inhibit cataract formation in young (50 g) rats fed a diet containing 50% galactose. Because of the higher levels of AR in these young rats and the inability of galactitol to be further metabolized, hypermature sugar cataracts rapidly form within fourteen days in this animal model. As a result this young galactose-fed rat is considered to be the "acid" test for ARIs because rapid lenticular penetration of ARI at concentrations that essentially inhibit all lenticular activity are required. Although a number of orally administered ARIs are known to inhibit sugar cataracts in this animal model, similar inhibition by topical administration had not been reported prior to these studies.

In the present studies each group, composed of six young rats, received a topical formation two times/day at 8 AM and 4 PM for two days. After two days of pretreatment, all six groups received diet containing 50% galactose (Bioserve, Frenchtown, N.J.), and similar topical treatment was continued. In all rats lens changes were evaluated at three day intervals by indirect opthalmoscope and portable handheld slit lamp, preceded by topical mydriasis with 1% tropicamide hydrochloride. Cataract severity was subjectively classified on a scale as follows: 0: clear; 0.5 suture accentuation; 1: equatorial vacuoles; 2: cortical opacities; and 3: hypermature.

Figure 2:
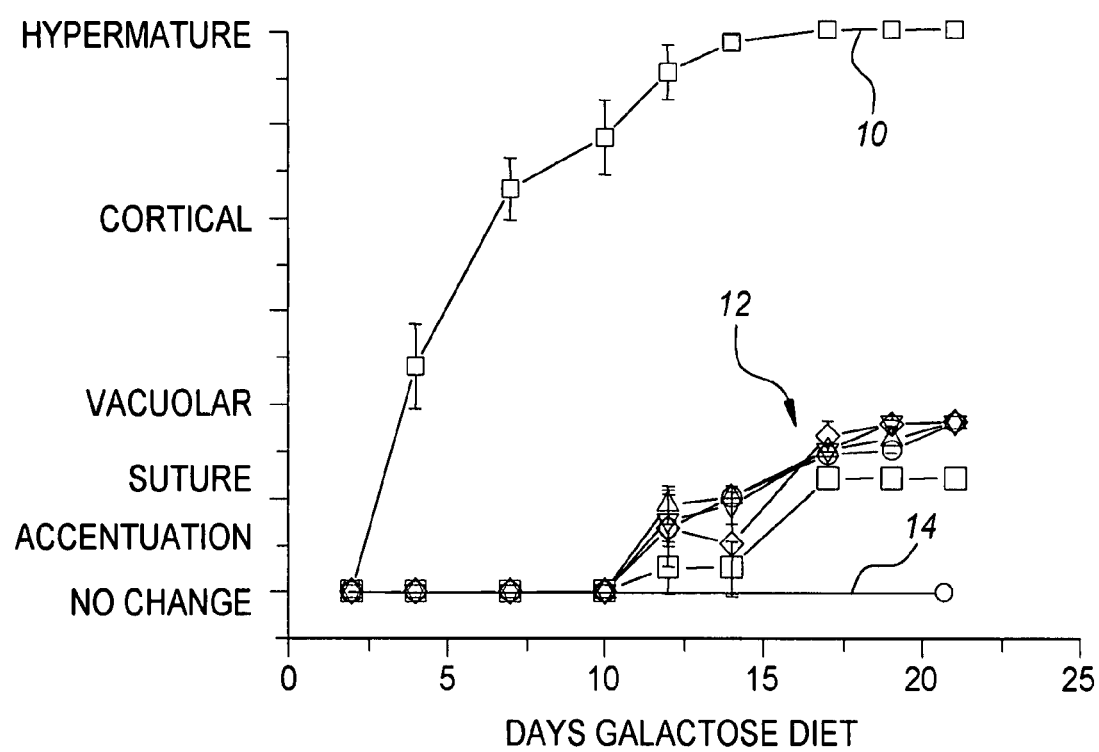
FIG. 2 is a chart showing the progression of sugar cataract formation in galactose-fed rats for the carriers of FIG. 1.

As shown in FIG. 1, the animal studies indicated that the highest lenticular levels of 2R-MS were obtained with the carbomer gel in the topical treatment of the present invention (designated as 6 or "K formulation" in FIG. 1), followed by 0.25% carbopol+0.25% HPMC (designated 5 in FIG. 1), 0.5% gellan gum (designated 3 in FIG. 1), 0.5% HPMC (designated 1 in FIG. 1), 0.25% carbopol (designated 4 in FIG. 1), and 0.5% xanthan gum (designated 2 in FIG. 1). As shown in FIG. 2, all topical formulations significantly reduced cataract formation in the young 50% galactose-fed rats compared to a control with no treatment, designated by curve 10. Lens changes were limited to an enhancement of the posterior sutures, suggestive of minor lens swelling, and a subsequent apparent demarcation between cortex and nucleus with/without suture enhancement with the first five formulations, designated by the cluster of curves 12. No lens changes were observed with the topical treatment of the present invention, designated by curve 14, and this correlated with the highest levels of lenticular 2R-MS observed in FIG. 1.

Example 3

Reversal of Cataract Damage

While prevention studies in rats indicate that sugar cataracts can be prevented when administered at the onset of galactosemia or diabetes, limited intervention studies suggest that reversing cataract formation can only be achieved at the early vacuolar stage of cataract formation. Since many dogs are diagnosed with diabetes mellitus after owners bring their dogs to veterinarians due to apparent lens changes, significant biochemical changes already have occurred. From a business perspective, a therapeutic treatment for sugar cataracts in dogs should not only arrest the progression of cataracts in dogs with clear lenses, but also reverse sugar cataracts in their early state. Therefore, a pilot study with topical treatment of the present invention was initiated to evaluate the ability of the topical treatment to ameliorate initial cortical cataract formation and its further progression.

Ten 6-month old male beagles, obtained from Marshall Farms, (North Rose, N.Y.), were utilized. All dogs received a daily 450 g diet containing 30% galactose with each dog individually fed at ca. 8 AM each day. Ophthalmic examinations were conducted at the onset of the study to establish that all dogs were free of lens opacities or retinal lesions. Subsequently, all eyes were examined monthly in a masked fashion by indirect opthalmoscope and handheld slit lamp by veterinary ophthalmologists. Examinations were performed on non-anesthetized animals and were preceded by mydriasis with topical 1% tropicamide HCl. Lens changes were documented at 0, 16 weeks and 25 weeks by photographs taken with a portable Nikon FS-3 Fundus Camera.

FIG. 3A shows representative sample photographs from two of the dogs treated with the topical carrier only, without an aldose reductase inhibitor, with the lenses of the first dog being shown in the top row and the lenses of the second dog being shown in the bottom row. The photographs in the left column were taken in vivo after fifteen weeks of galactose feeding, the photographs in the center column were taken in vivo at twenty-five weeks, after nine weeks administration of the topical carrier only, and the photographs in the third column were taken in vitro after twenty-six weeks, the lenses being placed over a grid after dissection.

Figure 3B:
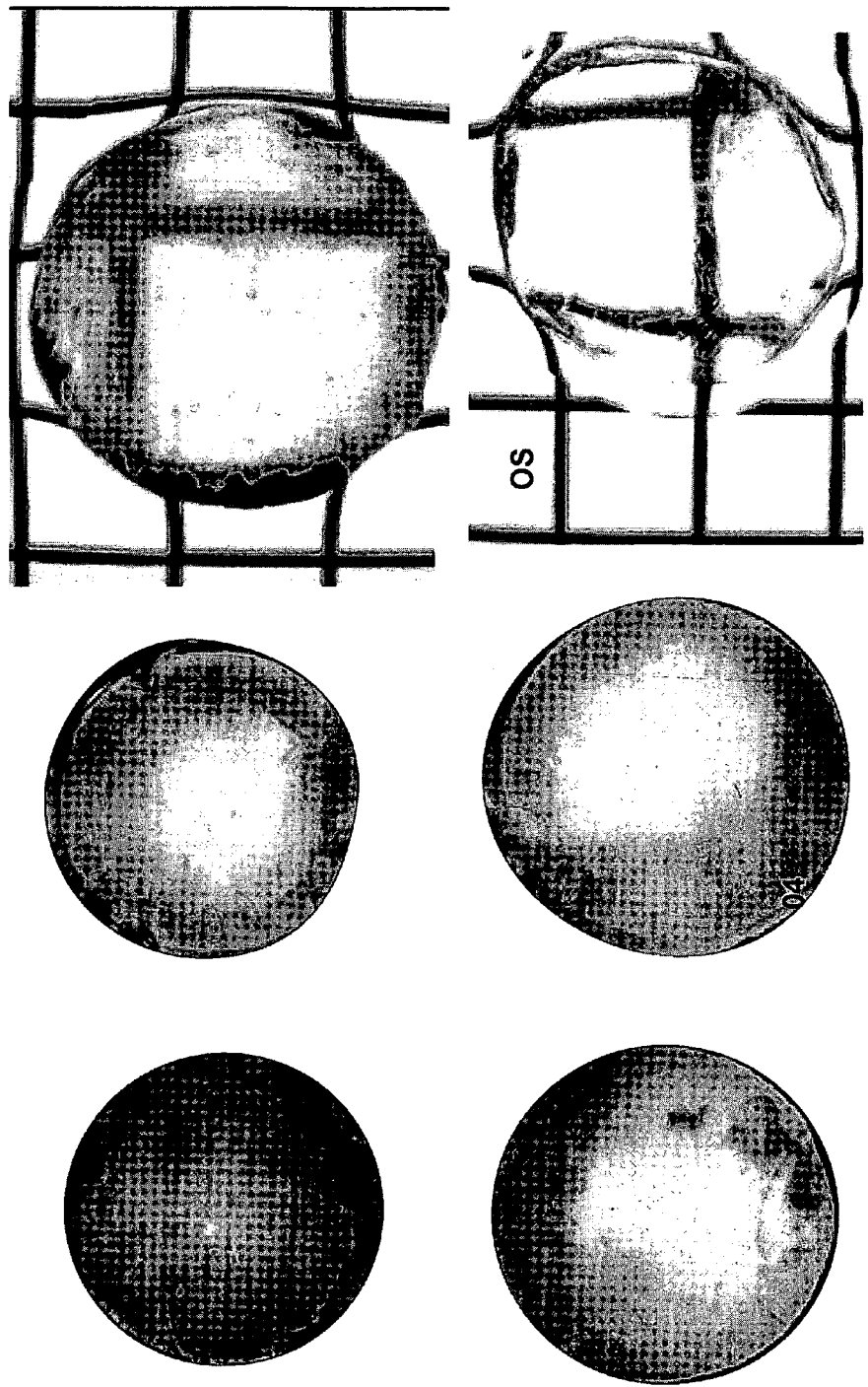
FIG. 3B shows photographs of the appearance of lenses in two dogs (the top and bottom rows respectively) after fifteen weeks of galactose feeding (first column), after nine weeks of administration of the topical treatment of the present invention, and the lenses placed over a grid after dissection at twenty-six weeks.

FIG. 3B shows representative sample photographs from two of the dogs treated with the topical treatment of the present invention, with 2R-methyl sorbinil, with the lenses of the first dog being shown in the top row and the lenses of the second dog being shown in the bottom row. The photographs in the left column were taken in vivo after fifteen weeks of galactose feeding, the photographs in the center column were taken in vivo at twenty-five weeks, after nine weeks administration of the topical treatment containing 2R-MS, and the photographs in the third column were taken in vitro after twenty-six weeks, the lenses being placed over a grid after dissection.

As the study progressed, suture accentuation was the earliest observed lens change, which appeared at four weeks of galactose feeding. This was followed at eight weeks by the appearance of vacuoles and by twelve weeks the appearance of superficial cortical opacities in all dogs. At sixteen weeks, bilateral cortical opacities were present in all dogs, as shown by the photographs in the leftmost columns of FIGS. 3A and 3B. Little apparent tapetal reflex from the flash of the portable fundus camera was present due to the density of the lens opacities. At that time, six randomly selected dogs received the topical treatment of the present invention with one drop per eye administered at ten minute intervals at 8 AM and 4 PM (four drops total/eye/day). The remaining four dogs were similarly administered vehicle (topical carrier without 2R-methyl sorbinil). Treatment was conducted for ten weeks.

Following administration of the topical treatment of the present invention, the tapetal reflex appeared to increase, suggesting that the density of lens opacities was reduced and/or lens clearing had occurred, as shown in the photographs in the center column of FIG. 3B. Further increases were observed after ten weeks, when the study was terminated. During the same time period, the apparent tapetal reflex in the four vehicle treated dogs was further reduced, as shown by the photographs in the center column of FIG. 3A. At the termination of the study, all vehicle-treated dogs had mature dense cataracts.

Following euthanasia at the completion of the study, the isolated lenses from each dog were placed over a lit surface with a grid and photographed. As shown by comparison of the photographs in the rightmost columns of FIGS. 3A and 3B, more of the grid was visible in the lenses from dogs treated with the topical treatment of the present invention.

Figure 4B:
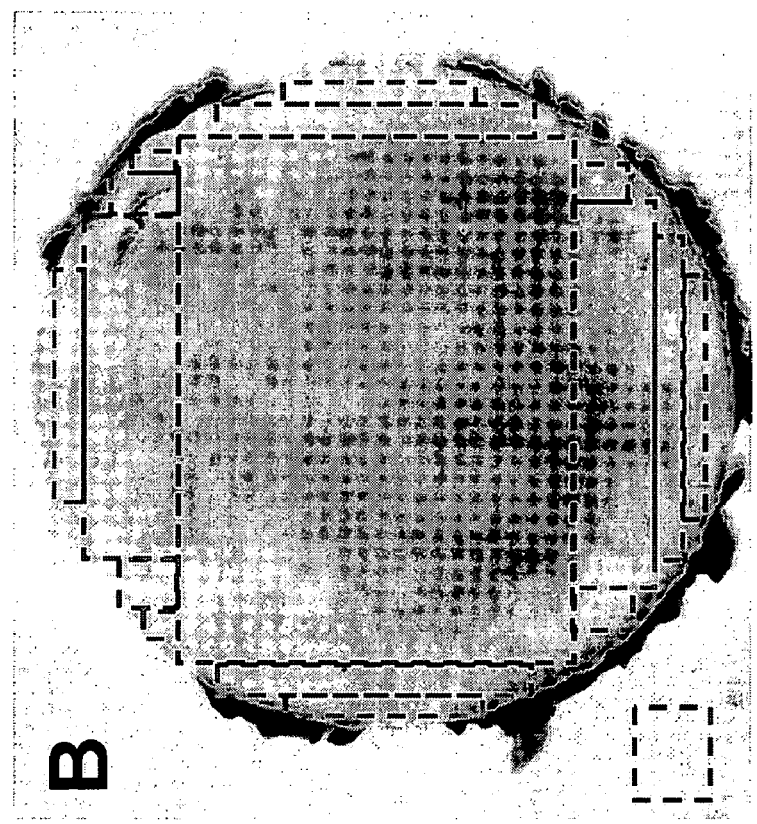
FIG. 4B shows the lens of FIG. 4A with the grid removed and with a series of rectangles showing sample areas of interest for software calculation of optical density.
Figure 4A:
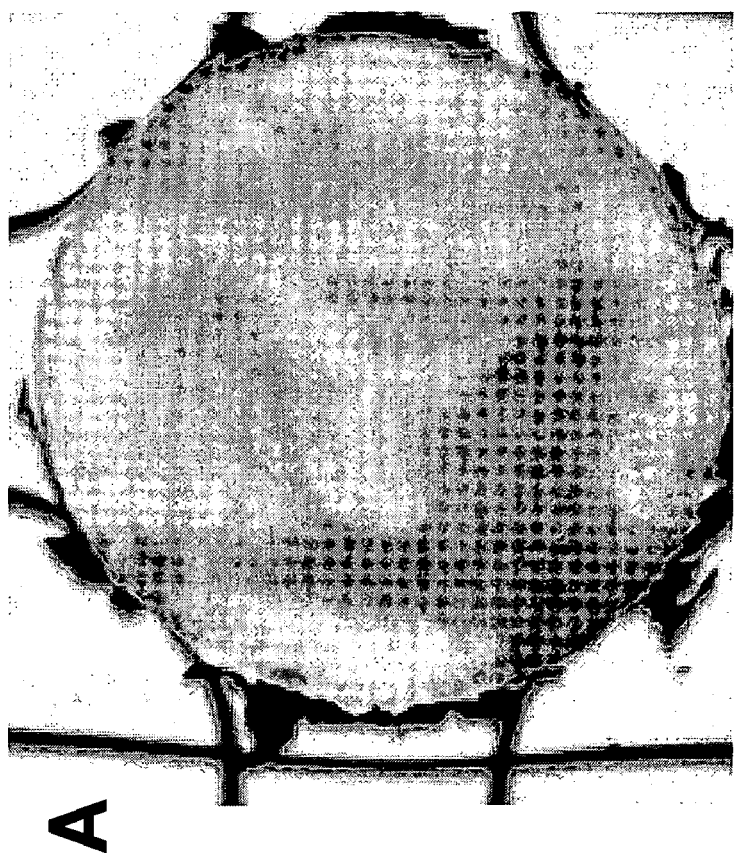
FIG. 4A shows an image of a cataractous lens placed over a grid for software calculation of optical density.
Figure 5A:
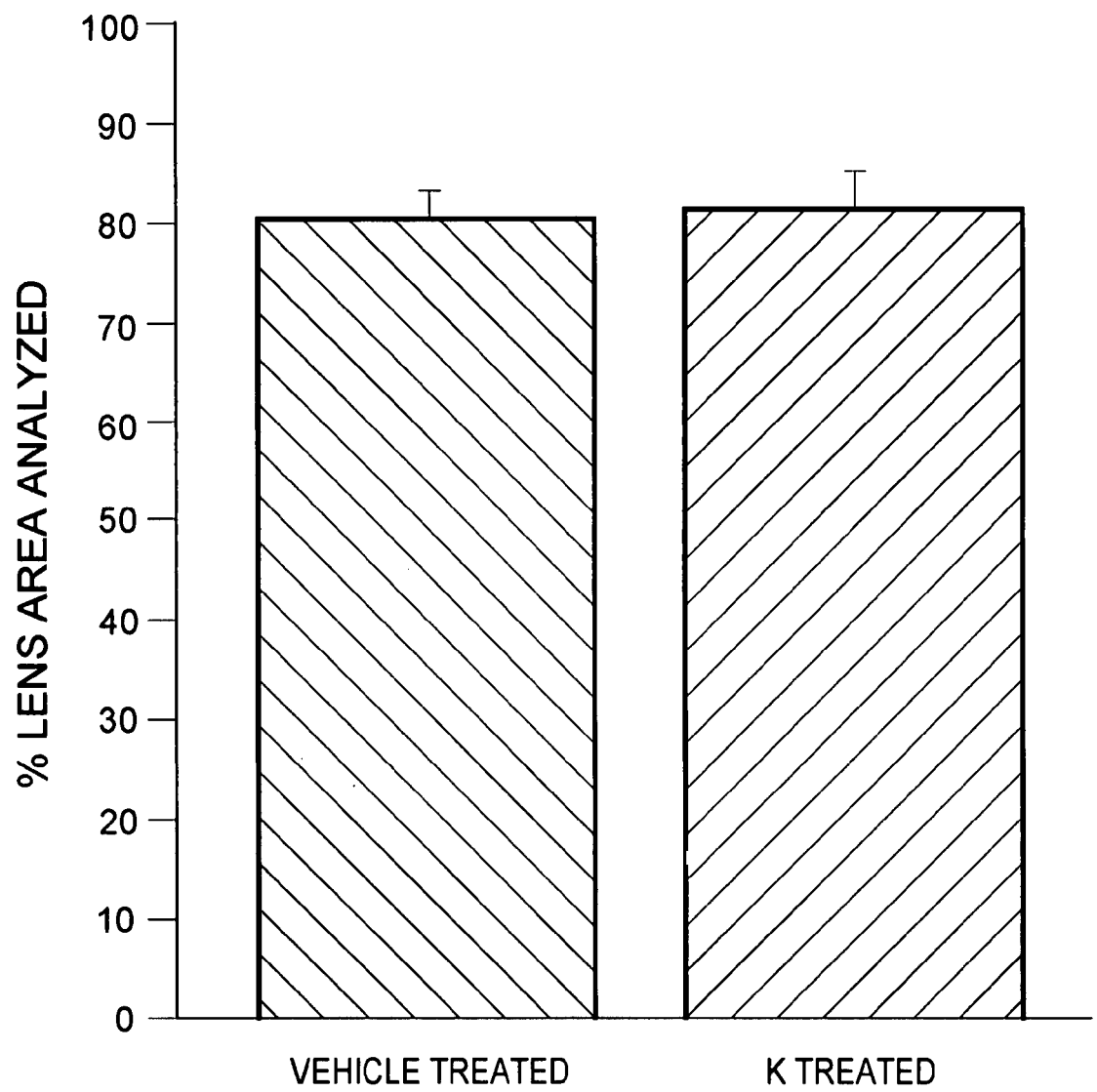
FIG. 5A is a chart showing the average area of lens sampled by optical density software in lenses administered a topical carrier only without an ARI and in lenses administered the topical treatment of the present invention, respectively.
Figure 5B:
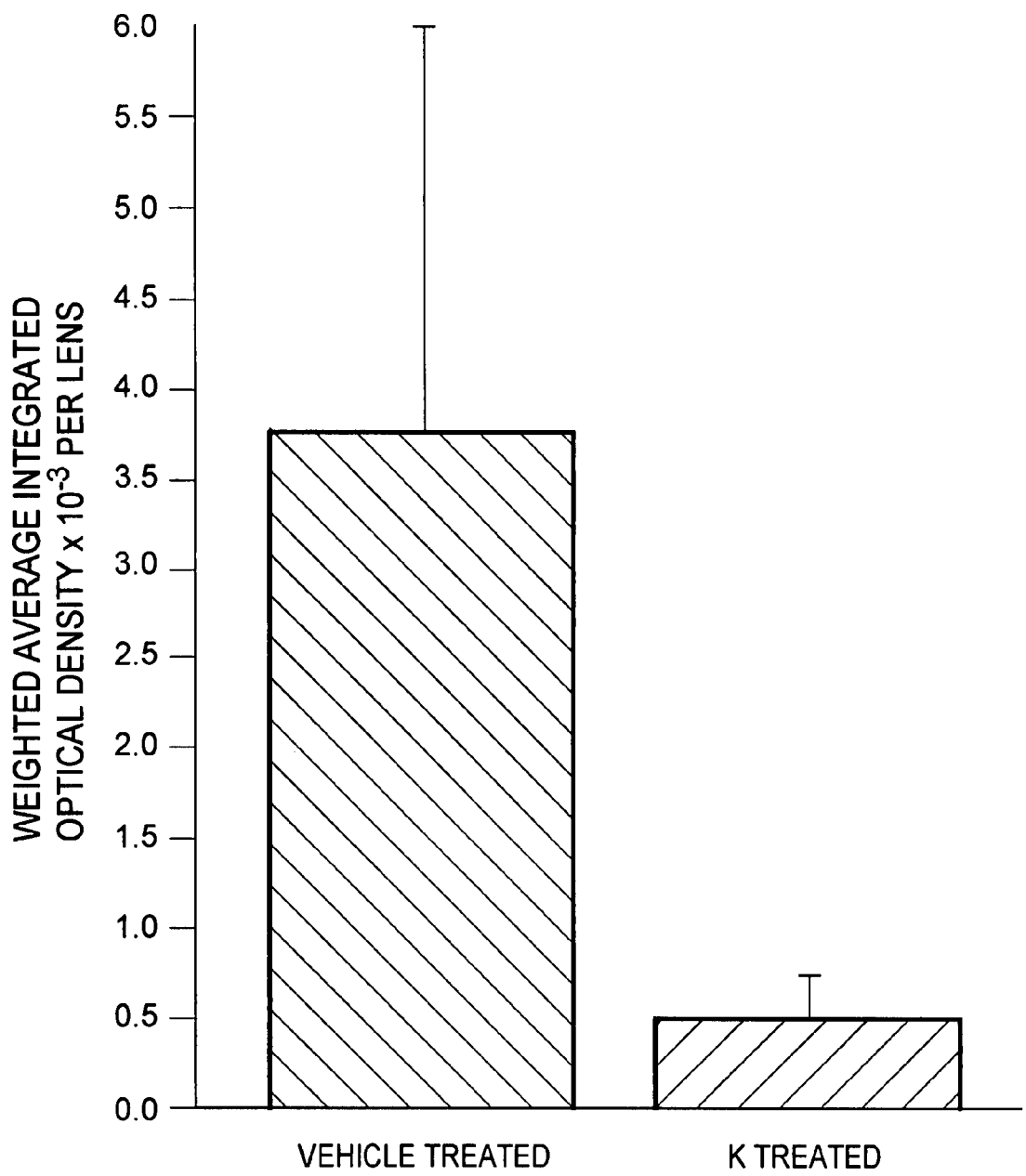
FIG. 5B is a chart showing the weighted average integrated optical density per unit of area as calculated by optical density software in lenses administered a topical carrier only without an ARI and in lenses administered the topical treatment of the present invention, respectively.

The lenses were further evaluated by computer software. As shown by the representative lens in FIGS. 4A and 4B, each lens was first photographed over a grid (FIG. 4A) and then with the lens removed (FIG. 4B). Without the grid, the inverted image gave greater detail. Lens density measurements were conducted on the inverted images with computer image analysis. Rectangular areas of interest (AOI) were constructed within each lens until the majority of the lens area was covered, as shown in FIG. 4B. The weighted average integrated optical density of the total AOIs was then obtained through pixel measurements. As summarized in FIGS. 5A and 5B, AOI analysis was conducted on equal areas of each lens. Comparison of the weighted average integrated optical density per area analyzed for the lenses from each group indicated that the opacities in the lenses treated with the topical treatment of the present invention (designated as K treated in the drawings) were significantly ($p \leq 0.05$) less dense than the vehicle treated lenses ($0.47 \pm 0.34 \times 10^{-3}$ versus $3.9 \pm 2.2 \times 10^{-3}$).

Figure 6A:
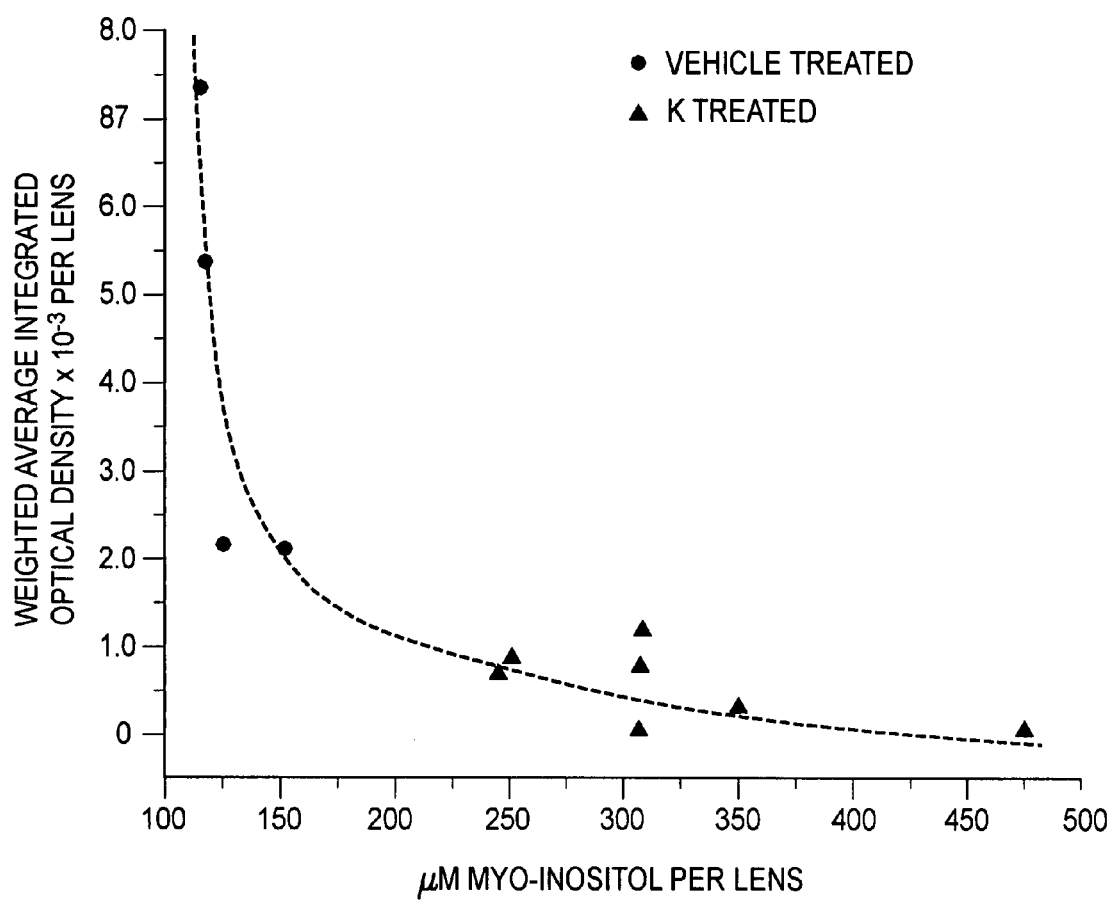
FIG. 6A is a chart showing weighted average integrated optical density per unit of area vs. myo-inositol level per lens in dogs treated with topical carrier only and with the topical treatment of the present invention, respectively.
Figure 6B:
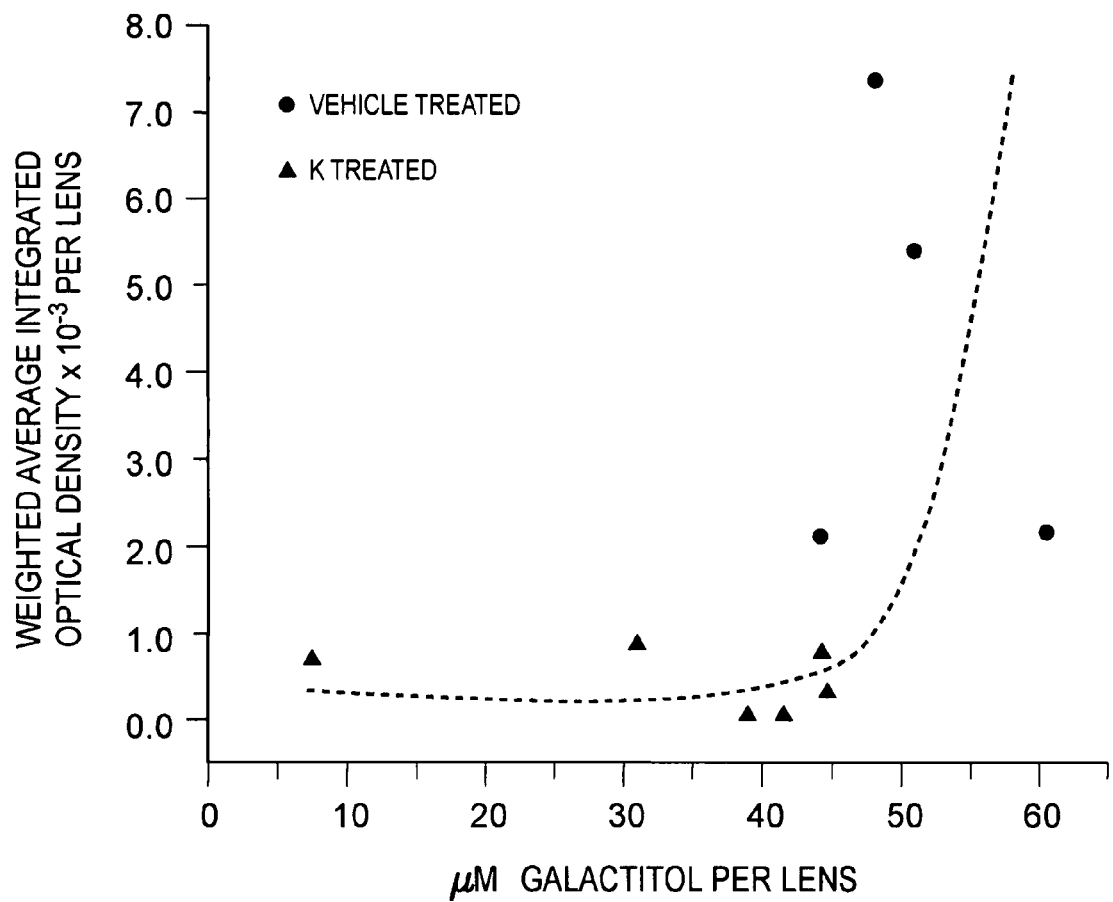
FIG. 6B is a chart showing weighted average integrated optical density per unit of area vs. galactitol level per lens in dogs treated with topical carrier only and with the topical treatment of the present invention, respectively.
Figure 6C:
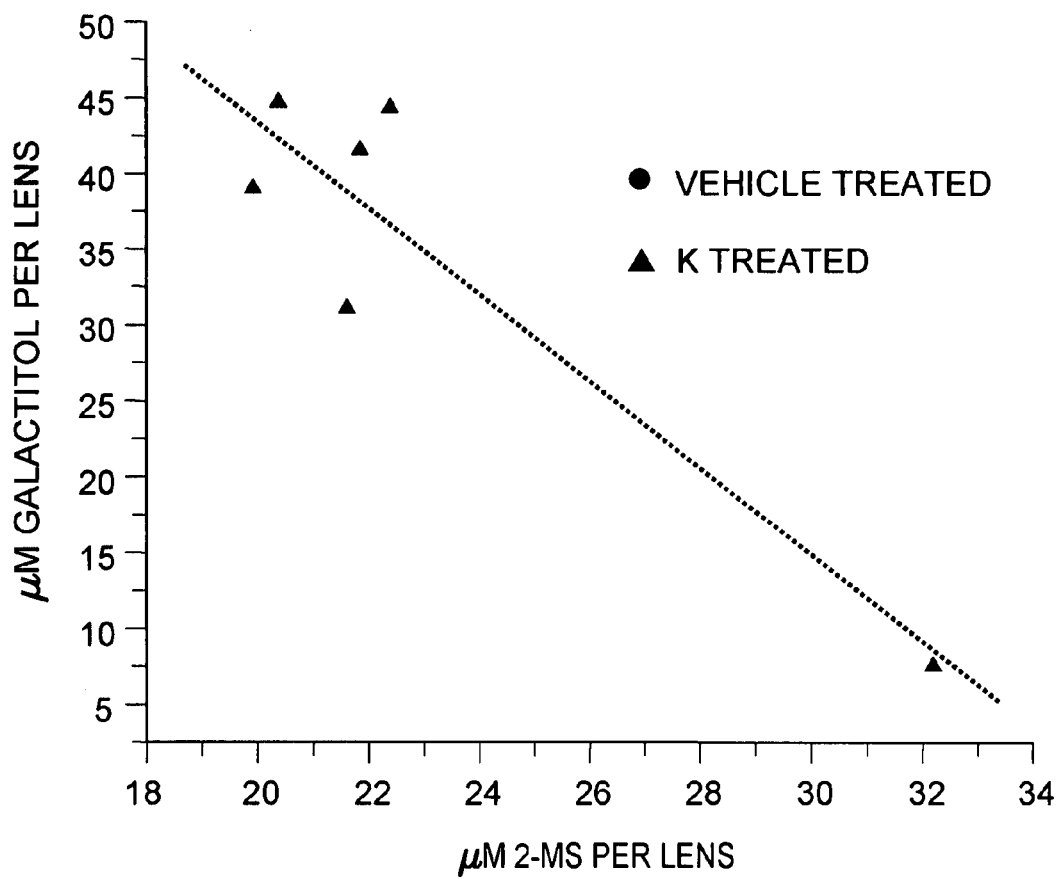
FIG. 6C is a chart showing galactitol levels vs. the level of the topical treatment of the present invention per lens in dogs treated with the topical treatment of the present invention.

Sugar analysis of each lens confirmed that cataract formation was less severe in the group treated with the topical treatment of the present invention (designated as K treated in FIGS. 6A-6C). Myo-inositol levels, which rapidly decrease with sorbitol or galactitol accumulation, were significantly ($p \leq 0.05$) higher in the K treated lenses ($311.0 \pm 89.4$ μM versus $105.0 \pm 18.0$ μM for the vehicle treated), indicating that AR activity was being inhibited. In contrast, galactitol levels of the vehicle treated group were only slightly higher than in the K treated group, with no significant difference between the two groups ($50.9 \pm 7.0$ μM per lens versus $34.7 \pm 14.2$ μM per lens). This correlates with the observed presence of mature cataracts in the vehicle treated group, which makes the lenses more permeable to polyols.

As summarized in FIGS. 6A-6C, lenticular 2R-MS levels were associated with lower levels of galactitol, and the lenses from the K treated dogs had lower optical densities, higher myo-inositol levels, and lower galactitol levels than those from the vehicle treated dogs. Moreover, the galactitol levels appeared to decrease with increasing 2R-MS levels.

Figure 7:
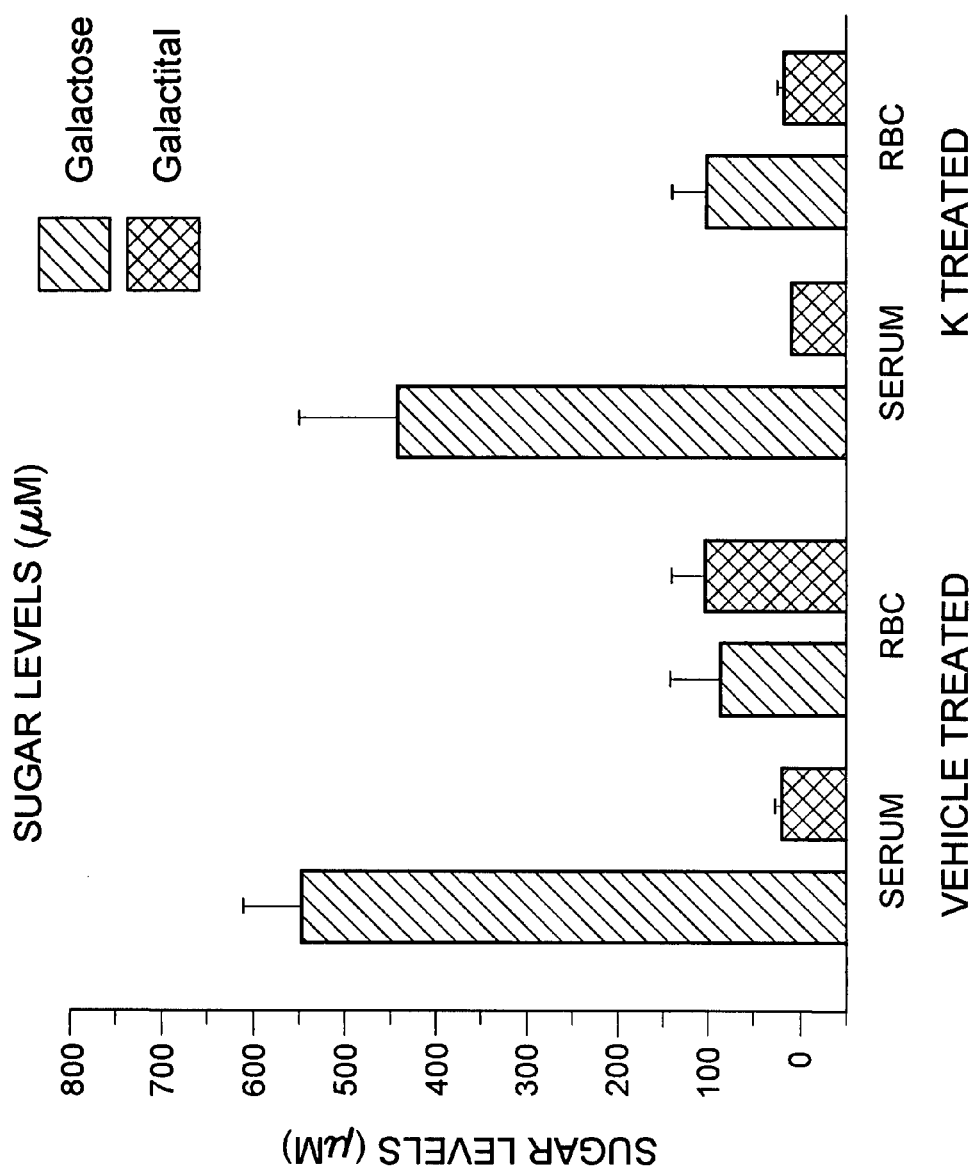
FIG. 7 is a chart showing the levels of galactose and galactitol in the serum and red blood cells of dogs treated with a topical carrier only without an ARI and with the topical treatment of the present invention, respectively.

No significant abnormalities in blood chemistry profiles, monitored at the beginning and end of the study, were observed, as shown in FIG. 7. All dogs were equally galactosemic, with no statistical difference between the K treated and vehicle treated groups observed with respect to serum galactose levels ($436 \pm 106$ versus $544 \pm 63.4$ μM), isolated red blood cell galactose levels ($108 \pm 42.4$ versus $95.7 \pm 30.2$ μM) or Hgb Alc levels ($4.9 \pm 0.1$ and $5.0 \pm 0.1$%). However, K treatment resulted in a significant ($p \leq 0.05$) decrease in red blood cell galactitol levels ($17.0 \pm 8.50$ versus $112.7 \pm 36.3$ μM), but not in total serum galactitol levels ($9.9 \pm 3.2$ versus $16.4 \pm 10.4$ μM). This suggests a slight systemic effect from topical application.

It is to be understood that the present invention is not limited to the embodiments described above, but encompasses any and all embodiments within the scope of the following claims.

We claim:

1. A topical composition for treatment of optical complications of diabetes in dogs, comprising:
   a topical carrier having by weight about 2.5% carbomer, 1.5% glycerin, 0.02% EDTA and 0.01% benzalkonium chloride, the balance being water; and
   an aldose reductase inhibitor mixed with the topical carrier to form an ophthalmic gel.

2. The topical composition according to claim 1, wherein said aldose reductase inhibitor has the formula:

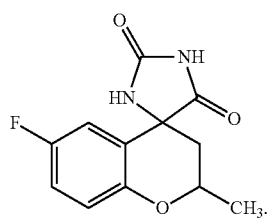

2-Methyl Sorbinil or a pharmaceutically acceptable salt thereof, the aldose reductase inhibitor being between 5% and 6% by weight of the ophthalmic gel.

3. The topical composition according to claim 1, wherein said aldose reductase inhibitor has the formula:

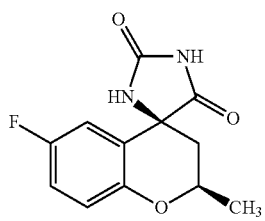

or a pharmaceutically acceptable salt thereof, the aldose reductase inhibitor being between 5% and 6% by weight of the ophthalmic gel.

4. A method for achieving an effect in a dog, comprising the step of administering an effective amount of the composition of claim 3 to the dog, wherein the effect is inhibiting the formation of diabetic cataracts.

5. A method for achieving an effect in a dog, comprising the step of administering an effective amount of the composition of claim 3 to the dog, wherein the effect is reversal of the formation of diabetic cataracts.

6. A method for achieving an effect in a dog, comprising the step of administering an effective amount of the composition of claim 3 to the dog, wherein the effect is: inhibiting the formation of diabetic cataracts; reversal of the formation of diabetic cataracts; reducing and reversing diabetic complications affecting the cornea, iris, ciliary bodies; or reducing complications resulting from diabetic retinopathy.

7. A method for achieving an effect in a dog, comprising the step of administering an effective amount of the composition of claim 1 to the dog, wherein the effect is inhibiting the formation of diabetic cataracts.

8. A method for achieving an effect in a dog, comprising the step of administering an effective amount of the composition of claim 1 to the dog, wherein the effect is reversal of the formation of diabetic cataracts.

9. A method for achieving an effect in a dog, comprising the step of administering an effective amount of the composition of claim 1 to the dog, wherein the effect is: inhibiting the formation of diabetic cataracts; reversal of the formation of diabetic cataracts; reducing and reversing diabetic complications affecting the cornea, iris, ciliary bodies; or reducing complications resulting from diabetic retinopathy.

10. A method of inhibiting and treating optical complications of diabetes in a dog, comprising topically administering between two and four drops daily of a composition having at least 5% by weight of an aldose reductase inhibitor emulsified in a carrier containing, by weight, about 2.5% carbomer, 1.5% glycerin, 0.02% EDTA and 0.01% benzalkonium chloride, the balance being water.

11. The method of inhibiting and treating optical complications of diabetes in a dog according to claim 10, wherein said aldose reductase inhibitor has the formula:

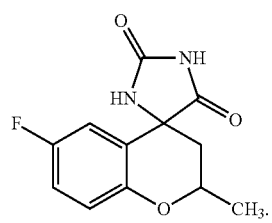

2-Methyl Sorbinil or a pharmaceutically acceptable salt thereof.

12. The method of inhibiting and treating optical complications of diabetes in a dog according to claim 10, wherein said aldose reductase inhibitor and said carrier form an ophthalmic gel, the aldose reductase inhibitor being between 5% and 6% by weight of the ophthalmic gel.

13. The method of inhibiting and treating optical complications of diabetes in a dog according to claim 10, wherein said aldose reductase inhibitor has the formula:

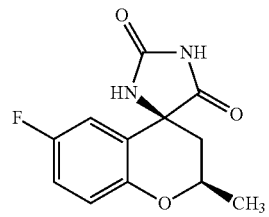

or a pharmaceutically acceptable salt thereof.

14. The method of inhibiting and treating optical complications of 2 diabetes in a dog according to claim 13, wherein said aldose reductase inhibitor and said carrier form an ophthalmic gel, the aldose reductase inhibitor being between 5% and 6% by weight of the ophthalmic gel.

* * * * *